United States Patent [19]

Dragan

[11] Patent Number: 4,963,093
[45] Date of Patent: Oct. 16, 1990

[54] DENTAL SYRINGE TIP AND SYRINGE HOLDER THEREFOR

[76] Inventor: William B. Dragan, 85 Burr St., Easton, Conn. 06612

[21] Appl. No.: 306,471

[22] Filed: Feb. 6, 1989

[51] Int. Cl.$^5$ .............................................. A61C 5/04
[52] U.S. Cl. ...................................................... 433/90
[58] Field of Search ........................................... 433/90

[56] References Cited

U.S. PATENT DOCUMENTS

| | | | |
|---|---|---|---|
| 2,381,785 | 8/1945 | Thompson | 433/90 |
| 3,900,954 | 8/1975 | Dragan | 433/90 |
| 4,682,950 | 7/1987 | Dragan | 433/90 |
| 4,767,326 | 8/1988 | Bennett et al. | 433/90 |

FOREIGN PATENT DOCUMENTS 2260515  9/1975  France ................................. 433/90

*Primary Examiner*—John J. Wilson
*Attorney, Agent, or Firm*—Arthur T. Fattibene

[57] ABSTRACT

This disclosure is directed to a dental syringe and a disposable syringe tip for use therewith, and more particularly to an improved syringe tip constructed to minimize the entrainment of air by the material being extruded and to provide a dentist with a maximum of visibility during use. The syringe tip includes a cylindrical body portion to define a reservoir that is provided with a conically shaped, closed front end and a full opening at the other end, which is adapted to be sealed by a displaceable piston. The closed front end is provided with an internal frusto-conical chamber disposed in communication with an angularly offset discharge nozzle having its passageway at the inner end thereof disposed contiguous to the blunt end of the internally disposed frusto-conical chamber; and the disposable piston having a frusto-conical end portion to complement the shape of the internal front end of the syringe tip to enhance the complete evacuation of the material disposed within the syringe tip without the entrainment of any air.

11 Claims, 1 Drawing Sheet

DENTAL SYRINGE TIP AND SYRINGE HOLDER THEREFOR

FIELD OF INVENTION

This invention relates to a dental syringe device, and more particularly to an improved syringe tip for use with a syringe holder of the type utilized to facilitate the placement of various dental materials in or on a tooth, such as composite dental filling materials, bonding materials, sealants, etchants and the like.

RELATED APPLICATIONS

This application relates to a design application S.N. 07/306,651 filed Feb. 6, 1989 for Dental Syringe Tip.

PROBLEM AND PRIOR ART

Dental syringes and syringe tips for use therewith have been known for some years. Such a dental syringe was initially disclosed in my U.S. Pat. No. 3,581,399. Other variations of such dental syringes and disposable syringe tips and capsules have been made the subject of other patents granted to me as evidenced by U.S. Pat. Nos. 3,900,954; 4.198,756; 4,682,950; 4,768,954; DES 289,682 and DES 292 825. Patents directed to similar dental syringes and disposable capsules for use therewith have also been granted.. together as, evidenced by U.S. Pat. Nos. 4,295,828; 4,330,280; 4,384,853; 4,391,590 and 4,767,326.

In utilizing syringe tips of the configuration disclosed in U.S. Pat. Nos. 4,330,280; 4,384,853: 4,391,590 and 4,767,326, which are characterized by a common and well known hemispherical end wall structure with offset discharge nozzle, it has been noted that in the filling of such syringe tip with a viscous material, there is a tendency to entrap air in the bulbous hemispherical end portion, and that the air tends to remain entrapped therein only to become entrained within the material as it is dispensed from the syringe tip upon the ejection thereof. The dental material that is generally dispensed by such capsules or syringe tip comprises a viscous composite resin dental filling material and the entrapment of any air within such material is considered to be highly detrimental to any tooth restoration made thereby. This is because the entrapment of any air in such composite resin filling material will result in voids being formed in the restoration, and which voids weaken and/or cause premature failure.

In restoring a tooth with a composite resin filling material, it is therefore desirable that the entrapment of any air therein be held to the absolute minimum so as to effect a final restoration that is free of any air voids. Another problem noted with capsules or syringe tips having the bulbous hemispherical front end configuration with the offset discharge nozzle of the type disclosed in U.S. Pat. No. 4,391,590 was that visibility was obscured when placing the material with such syringe tip configuration in deep small areas. This was due to the bulbous hemispherical end obscuring the site where the material was to be placed: as the discharge nipple or orifice through which the material was extruded would be obscured thereby.

Also, there has been a growing tendency in the art to formulate dental composite resin filling materials with a heavier or more viscous consistency. With such heavy bodied materials, it is imperative that the syringe tips for dispensing such material be made to withstand the tremendous pressures that occur when such viscous materials are to be extruded therefrom. Heretofore, the known capsules, such as disclosed in U.S. Pat. No. 4,391,590 and 4,767,326 were made with a uniform wall thickness throughout, and thus did not compensate for the resistance of pressure in those areas where the pressures were maximized during an extruding operation; e.g. in the closed end of the capsule or syringe tip.

OBJECTS

An object of this invention is to provide an improved syringe tip for use with a dental syringe having a construction that prohibits the entrapment and/or entrainment of air in the material as it is being extruded from the syringe tip.

Another object of this invention is to provide an improved syringe tip constructed so as to allow better visibility for the dentist during the delivery of the material to a tooth.

Another object of this invention is to provide an improved syringe tip having a reinforced front end to better withstand the pressures incurred during an extruding operation.

Another object of this invention is to provide an improved syringe tip construction having an angularly disposed discharge nozzle having its inlet disposed contiguous to an internal front end wall of the syringe tip so as to minimize or prohibit the entrapment of air within the syringe tip.

SUMMARY OF THE INVENTION

The foregoing objects and other features and advantages are attained by an improved syringe tip construction that comprises a generally cylindrical body portion to define a reservoir for containing a predetermined amount of dental material to be dispensed therefrom. One end of the body portion is provided with a full open end through which it can be readily filled with the dental material to be dispensed, e.g. a composite resin filling material. The other end of the cylindrical body portion is closed by a conically shaped tip end that tapers inwardly toward the front end of the syringe tip, and which conically shaped tip defines an internal frusto-conical chamber disposed in open communication with the reservoir and in axial alignment therewith. The front end of the internal chamber is provided with a blunt end wall and a discharge nozzle is angularly disposed relative to the conical closed end so that the passageway extending through the discharge nozzle is provided with an inlet disposed contiguous to the internal blunt front end wall of the syringe tip. A displaceable piston is provided to seal the full open end of the body portion, and which piston is provided with a frusto-conical end portion to complement the shape of the internal frusto-conical chamber at the front end of the syringe tip so as to insure complete evacuation of the material within the syringe tip free of any air entrainment. C'rcumscribing the open end of the body portion is a laterally extending flange: and a sealing cap may be provided to seal the discharge orifice of the angularly disposed nozzle. The improved syringe tip is adapted to be used with a syringe construction having a barrel for receiving the syringe tip and having a plunger for effecting the displacement of the piston for extruding the material out of the syringe tip.

FEATURES

A feature of this invention resides in the provision of an improved dental syringe tip having a cylindrical reservoir portion for containing a predetermined supply of a dental material that is in open communication with an axial aligned frusto-conical internal chamber disposed adjacent an angularly offset discharge nozzle arranged to prohibit entrapment and/or entrainment of air by the material to be extruded therefrom.

Another feature of this invention resides in an improved dental syringe tip having a conical tip with an angular offset nozzle for enhancing the visibility of the dentist in placing of the material being dispensed.

Another feature resides in the provision of an improved dental syringe tip in which the front end of the syringe is reinforced to withstand the induced pressures thereon during an extruding operation.

Another feature resides in the provision of an improved dental syringe tip and displaceable piston arranged to insure total evacuation of the material to be dispensed thereby.

Other features and advantages will become more readily apparent when considered in view of the drawings and description thereof in which.

DETAIL DESCRIPTION

Figure 1:
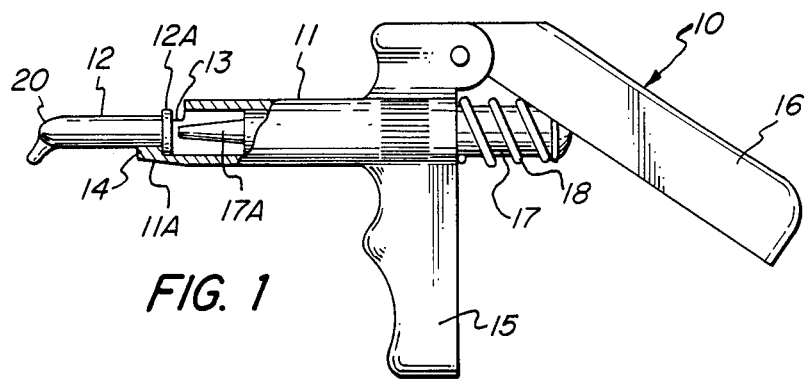
FIG. 1 is a side elevation view, shown partly in section of a dental syringe and dental syringe tip for use therewith that embodies the invention.

Referring to the drawings, FIG. 1 illustrates a dental syringe 10 of a type disclosed in my prior issued U.S. Pat. No. 4,198,756. Such dental syringe 10 comprises essentially an elongated barrel 11 having a front end portion 11A adapted to detachably hold the improved dental syringe tip 12, as will be hereinafter described. In the illustrated embodiment, the front end of the barrel 11 is provided with a cut-away portion to define a breech opening 13 in the upper part of the barrel. The front portion of the barrel, which is not cut-away, is provided with an inturned flange as indicated at 14 to define an internal shoulder to engage the flange of the syringe tip as will be hereinafter described. Connected to the barrel adjacent the other end thereof is a handle or finger grip member 15. Pivotably connected to the handle 15 is an actuating lever 16 which is disposed in bearing relationship with a plunger 17 which is slidably disposed within the barrel 11. A spring interposed about the end of the plunger 17 maintains the plunger 17 in a normally retracted position as shown in FIG. 1. The front end of the plunger 17 is provided with a projection 17A arranged to engage the displaceable piston of the syringe tip 12, as will be hereinafter described, to effect the extrusion of the material within the syringe tip 12 when the lever 16 is actuated.

It will be understood that the front end of the barrel is sized or proportioned so as to frictionally retain the rear portion off the syringe tip in the notched opening 13 formed therein. As shown, the shoulder or inturned flange 14 engages the flange 12A of the syringe tip to prevent axial displacement of the syringe tip 12 during actuation of the syringe 10. The arrangement is such that the syringe tip is forced into and held in place by the seat defined at the notched end of the barrel 10. To achieve a suitable friction fit of the syringe tip in the front end of the barrel, the cut-out 13 is formed so that the circumscribing side walls to the barrel extend about the circumference of the syringe tip slightly more than 180°.

While the syringe illustrated comprises a so-called "gun type" syringe, it will be understood that other syringe constructions can be utilized to practice the invention, e.g. such as disclosed in my prior U.S. Pat. Nos. 3,900,954 or 3,581,399.

Figure 3:
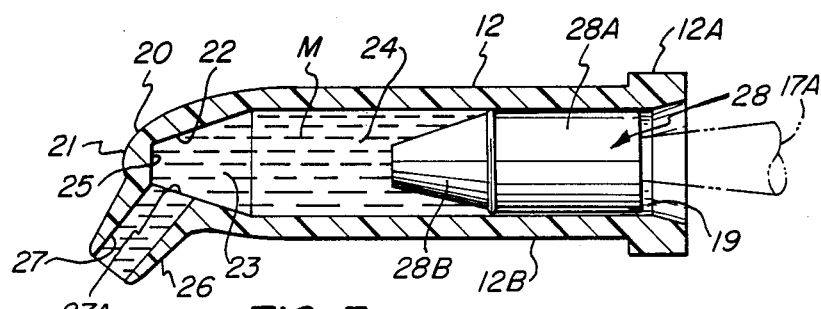
FIG. 3 is a sectional view of the syringe tip illustrated in FIGS. 1 and 2.
Figure 4:
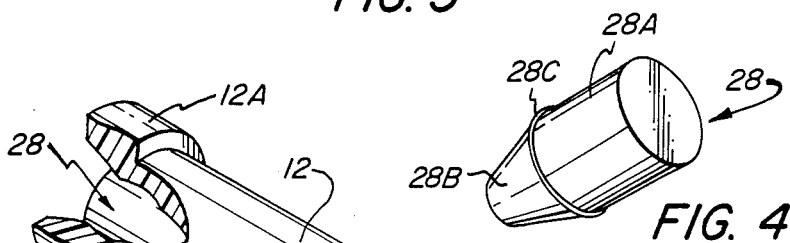
FIG. 4 is a detail perspective view of the piston sealing the open end of the syringe tip.
Figure 2:
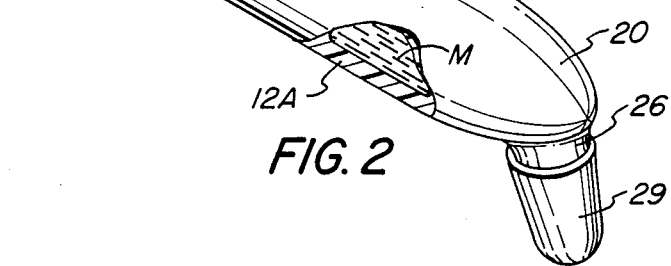
FIG. 2 is a perspective view of the improved syringe tip.

In accordance with this invention, the improved syringe tip 12 comPrises a generally cylindrical body portion 12B which is fully open at one end as indicated at 19, and which is provided with a closed end 20 at the other end thereof. As shown, the closed end is generally of a round conical shape which tapers inwardly toward the closed apex end 21. The front conical end 20 is provided with a frusto-conical internal wall 22 to define an internal frusto-conical internal chamber 23 which is axially disposed and in open communication with the reservoir portion defined by the cylindrical body portion 12B. As best seen in FIG. 3, the inner frusto-conical chamber 23 terminates in a blunt end wall 25. Due to the roundness of the outer wall surface of the front conical end 20 and the angular interior surface 22 of the conical chamber 23, it will be noted that the wall thickness of the conical front end varies, whereby the thickness of the front end wall progressively increases toward the medium of the internal frusto-conical chamber. The arrangement is such that the variable thickness of the syringe tip wall at the front end thereof functions to reinforce the syringe tip so as to resist the pressures which tend to build up on the front end wall as the material is being extruded from the syringe tip. As the manufacturers of dental composite resin materials are producing a more viscous composite resin, the problem of pressure build-up on the end walls of a syringe tip is aggravated. Thus, the described construction renders the syringe tip 12 compatible for use with the most viscous of known dental composite resin materials.

Formed as an integral part of the syringe tip is a discharge nozzle 26 which is angularly disposed relative to the longitudinal axis of the body portion 12 that defines the reservoir 24 for containing the dental material M. As shown, the nozzle 26 is provided with a passageway 27 that is disposed in communication with the internal conical chamber portion 23. The angulation of the passageway is such that its inlet end 27A is disposed immediately adjacent the blunt end wall 25, so that no portion of the frusto-conical chamber 23 extends forwardly of the inlet 27A of the nozzle passageway 27 that can form a pocket to entrap air which would ultimately be entrained in the material being extruded.

In accordance with this invention, the open end 19 of the body portion is sealed by a displaceable piston 28. In the illustrated embodiment, the piston 28 includes a rear cylindrical portion 28A sized to be slidably received within the body of the syringe tip and a connected frusto-conical tip portion 28B. The frusto-conical tip 28B of the piston is sized so as to closely conform to the shape of the internal conical chamber 23 so as to insure maximum evacuation of the material M disposed within the syringe tip. At the base portion of the piston tip 28B, the piston 28 may be provided with one or more circumscribing ribs or wipers 28C to provide a positive seal between the piston 28 and the internal wall of the syringe tip so as to prevent any back flow of the material M during an extruding operation.

Preferably, the syringe tip described is formed of a molded plastic material which may comprise 101 Zytel nylon, or other suitable plastic materials such as polypropolene, etc., depending upon the nature of the material to be extruded therefrom.

The syringe tip may also be suitably colored so as to identify the type of material contained therein or be rendered light resistant or light opaque for use with light activated materials which are currently in vogue. Also, the syringe tips may be preloaded with suitable materials and sealed by means of an end cap 29 placed over the discharge orifice defined by the nozzle 26.

Loading of the syringe tip 12 described can be readily effected by inserting the material through the full open end 19 thereof. With the construction described, it will be apparent that any air confined within the syringe tip during a loading operation will be vented or forced out of the nozzle tip 26, and no entrapment of air can occur when the syringe tip is fully loaded. In the event the syringe tip is only partically loaded with dental material M, any air disposed between the material and the front end of the tip will be evacuated before the material begins to extrude. Thus, there are no entrapped air pockets by which air can be entrained in the dental material during an extrusion operation.

The conical shaped tip as described further enhances the visibility for the dentist when delivering the composite material to a tooth; as the discharge nozzle is not obscured. Also, since dentists inherently have to work in very close or small areas, the conical tip configuration provides better access as well as better visibility in such situations. The trucated or frusto-conical internal chamber at the closed end of the syringe tip further allows better direction in funneling the material to be extruded toward the discharge nozzle, thereby minimizing the resistive forces that occur with very viscous type materials.

While the invention has been described with respect to a particular embodiment thereof, variations and modifications may be made without departing from the spirit or scope of the invention.

What is claimed is:

1. A syringe tip for use in a dental syringe for the placement of a predetermined amount of a viscous dental composite resin filling material in a tooth to form a tooth restoration comprising
    a body portion having a generally cylindrical shape to define a reservoir portion for containing a predetermined amount of dental filling material.
    said body portion having an opening co-extensive to the cylindrical shape of said reservoir portion at one end thereof,
    a laterally extending flange circumscribing said opening,
    and said body portion having a tapering closed end at the other end thereof disposed in axial alignment with the axis of said body portion,
    said tapering closed end having an internal conically shaped wall surface tapering toward said closed end terminating in a blunt internal end wall,
    said internal conically shaped wall surface defining an internal frustro conical chamber being disposed in open communication with and forming a continuation of said reservoir portion,
    and a discharge nozzle angularly disposed relative to said closed end,
    said discharge nozzle including a passageway through which the material contained in said internal frustro conical chamber and reservoir portion is adapted to be extruded,
    and a displaceable piston for sealing the open end of said reservoir portion; said displaceable piston having a conical front end complementing said internal conically shaped wall surface.

2. A syringe tip as defined in claim 1 wherein said passageway includes an inlet end and an outlet end, said inlet end being disposed immediately adjacent said blunt internal end wall.

3. A syringe tip for use in a dental syringe for the placement of a dental composite resin filling material for forming a tooth restoration comprising
    a body portion having a cylindrical configuration defining a reservoir portion,
    said body portion having an opening formed at one end that is substantially co-extensive to the diameter of said reservoir portion, a laterally extending flange circumscribing said opening formed at one end, and said body portion being closed at the other end thereof,
    said closed end having an internal tapering wall co-axially disposed with said reservoir portion, and terminating in a blunt internal end wall to define an internal frustro-conical chamber axially disposed and in open communication with said reservoir portion,
    a discharge nozzle angularly disposed relative to said closed end,
    said discharge nozzle including a passageway disposed in communication with said closed end,
    said passageway having an inlet end disposed contiguous to said blunt end wall,
    and a displaceable piston for sealing said opening, said displaceable piston including a cylindrical rear portion and a conical front portion, said conical front portion complementing the conical shape of said internal surface of said closed end.

4. A syringe tip for use in a dental syringe for the placement of a dental filling material comprising
    a body portion having a cylindrical configuration defining a reservoir portion,
    said body portion having an opening formed at one end that is substantially co-extensive to the diameter of said reservoir portion, and said body portion being closed at the other end thereof,
    said closed end having an internal tapering wall co-axially disposed with said reservoir portion,
    said closed end terminating in a blunt internal end wall,
    a discharge nozzle angularly disposed relative to said closed end,
    said discharge nozzle including a passageway disposed in communication with said closed end,
    said passageway having an inlet end disposed contiguous to said blunt end,
    and a displaceable piston or sealing said opening,
    wherein said dispalceable piston includes a cylindrical rear portion and a conical front portion, said conical front portion complementing the conical shape of said internal surface of said closed end.

5. A syringe tip as defined in claim 4 wherein said closed end has an outer wall surface that tapers inwardly.

6. A syringe tip as defined in claim 5 wherein the thickness between the inner and outer surfaces of said closed end varies.

7. A syringe tip as defined in claim 6 wherein the thickness of the closed end progressively increases toward the medium portion thereof.

8. A syringe tip as defined in claim 4 and including a circumscribing wiper on said displaceable piston.

9. A syringe tip as defined in claim 8 wherein said wiper is disposed between said rear portion and front portion of said piston.

10. A syringe tip for use with a dental syringe for the placement of a predetermined amount of a dental material in a tooth comprising a body portion having a generally cylindrical shape to define a reservoir portion for containing a predetermined amount of a dental material, and said body portion terminating in a closed end portion that tapers inwardly toward said closed end thereof, said closed end portion defining an internal conically shaped chamber axially disposed relative to said reservoir portion, said conically shaped internal chamber tapering inward toward said closed end to define an inner blunt end wall surface disposed normal to the axis of said reservoir portion, a discharge nozzle angularly disposed relative to said closed end, said discharge nozzle having a passageway disposed in communication with said closed end, said passageway having an inlet disposed contiguous to said blunt end wall, said body being open at its other end, and a displaceable piston for sealing the open end, said displaceable piston having a frusto conical tip end to complement the internal chamber of said closed end.

11. A syringe tip for use in a dental syringe for the placement of a dental material in or on a tooth comprising a syringe body having a cylindrical shape to define a reservoir portion, said syringe body having a full opening at one end thereof, and a tapering sealed end at the other end thereof, a laterally extending flange circumscribing said full opening, said tapering sealed end having an exterior rounded conical surface and a conical interior surface to define an internal conically shaped chamber disposed in axial alignment with said reservoir portion, said internal conically shaped chamber tapering inwardly toward said sealed end, and terminating in a blunt end wall, a pre-determined amount of dental material disposed in said reservoir portion, a discharge nozzle angularly disposed relative to said sealed end, said nozzle having a passageway extending therethrough, said passageway having an inlet end disposed in communication with said conically shaped chamber and contiguously disposed to said blunt end whereby the plane of said blunt end forms a juncture with said inlet, a displaceable piston closing said full opening to seal said material within said reservoir portion, said piston including a frusto-conical tip complementing the shape of said internal conical chamber so as to insure maximum evacuation of said material upon the displacement of said piston, and a sealing cap fitted over the end of said discharge nozzle.

* * * * *